United States Patent [19]

Murtha

[11] 4,169,857

[45] Oct. 2, 1979

[54] SEPARATION OF CYCLOHEXYLBENZENE-CYCLOHEXANONE-PHENOL-CONTAINING MIXTURES BY HYDROGENATION AND DISTILLATION

[75] Inventor: Timothy P. Murtha, Bartlesville, Okla.

[73] Assignee: Phillips Petroleum Company, Bartlesville, Okla.

[21] Appl. No.: 948,837

[22] Filed: Oct. 5, 1978

[51] Int. Cl.$^2$ .................. C07C 45/24; C07C 7/04; C07C 45/00
[52] U.S. Cl. .................. 260/586 P; 260/586 R; 568/798; 585/807; 585/841; 203/32
[58] Field of Search .......... 260/586 P, 586 R, 674 H; 568/798; 203/65

[56] References Cited

U.S. PATENT DOCUMENTS

| | | | |
|---|---|---|---|
| 2,857,432 | 10/1958 | Joris | 260/586 P |
| 2,950,320 | 8/1960 | Vandenberg | 260/586 R |
| 4,021,490 | 5/1977 | Hudson | 260/586 R |
| 4,092,360 | 5/1978 | Van Peppen et al. | 260/586 P |
| 4,115,204 | 9/1978 | Murtha et al. | 260/586 R |
| 4,120,902 | 10/1978 | Wu | 260/586 P |

*Primary Examiner*—Norman Morgenstern

[57] ABSTRACT

A cyclohexylbenzene-cyclohexanone-phenol-containing mixture, for example as obtained by the cleavage of cyclohexylbenzene hydroperoxide, is separated by first catalytically hydrogenating selectively the phenol in the mixture, resulting in a mixture of cyclohexylbenzene, which is unchanged, and cyclohexanone; the thus obtained mixture is subjected to fractional distillation to obtain cyclohexylbenzene which can be returned as to a process for the production of cyclohexylbenzene hydroperoxide, and cyclohexanone.

5 Claims, No Drawings

SEPARATION OF CYCLOHEXYLBENZENE-CYCLOHEXANONE-PHENOL-CONTAINING MIXTURES BY HYDROGENATION AND DISTILLATION

This invention relates to the separation of a mixture containing cyclohexylbenzene, cyclohexanone and phenol. In one of its aspects the invention relates to a process for the recovery, unconverted, of cyclohexylbenzene contained in a mixture of it together with phenol and cyclohexanone. In another of its aspects the invention relates to a process for the recovery of cyclohexylbenzene from a mixture as herein described so that the cyclohexylbenzene can be converted to cyclohexylbenzene hydroperoxide.

In one of its concepts the invention provides a process for the separation of cyclohexylbenzene-cyclohexanone-phenol-containing mixture by steps which comprise subjecting said mixture to conditions of hydrogenation adapted to convert phenol to cyclohexanone, without however converting the cyclohexylbenzene, then subjecting the mixture thus obtained containing essentially cyclohexylbenzene and cyclohexanone to fractional distillation to separate cyclohexylbenzene on the one hand and cyclohexanone on the other as separate streams. In another of its concepts the invention provides steps as just described together with conditions suited to carry out the same.

Cyclohexylbenzene can be converted to phenol and cyclohexanone via cyclohexylbenzene hydroperoxide. The acid catalyzed cleavage of cyclohexylbenzene hydroperoxide in the presence of unoxidized cyclohexylbenzene results in a mixture of cyclohexylbenzene, phenol, and cyclohexanone. This mixture is difficult to separate by conventional distillation techniques because phenol and cyclohexanone form an azeotrope (boiling point 184° C. at atmospheric pressure) containing about 72 weight % phenol. Cyclohexylbenzene codistills with this azeotrope and also codistills with phenol.

I have now conceived a process and conditions therefor, permitting the ready recovery of cyclohexylbenzene, unchanged, for further use to prepare cyclohexylbenzene hydroperoxide. The process, steps and conditions are as here described.

It is an object of this invention to separate a mixture containing cyclohexylbenzene, cyclohexanone, and phenol. It is a further object of this invention to recover cyclohexylbenzene from a mixture containing it together with cyclohexanone and phenol. It is a further object of this invention to provide a process for the hydrogenation of phenol in a mixture containing it together with cyclohexylbenzene and cyclohexanone. It is a further object of this invention to separate cyclohexylbenzene from a mixture containing it in presence of a phenol-cyclohexanone azeotrope.

Other aspects, concepts, objects and the several advantages of this invention are apparent from a study of this disclosure and the appended claims.

According to the present invention, broadly described, cyclohexylbenzene is recovered from a mixture containing it together with phenol and cyclohexanone by subjecting the mixture to hydrogenation conditions under which substantially only the phenol is converted to cyclohexanone, the cyclohexylbenzene remains essentially unchanged, following which the mixture thus obtained now containing cyclohexylbenzene and cyclohexanone is subjected to distillation to separate the same into its essential components.

In the practice of this invention, any combination of phenol with cyclohexanone and cyclohexylbenzene can be utilized as the feed mixture. The acid catalyzed cleavage of cyclohexylbenzene hydroperoxide in unoxidized cyclohexylbenzene yields a mixture of phenol, cyclohexanone and cyclohexylbenzene. It is within the scope of this invention to remove by suitable methods a portion of any of the components from this mixture before the hydrogenation reaction of this invention. For example, any excess of cyclohexanone over the quantity present in the azeotrope can be first distilled from the mixture as essentially pure material. Since cyclohexylbenzene codistills with the phenol-cyclohexanone azeotrope in quantities of about 2 to about 10 wt. %, any excess of cyclohexylbenzene over that amount can be separated by fractional distillation with the phenol-cyclohexanone mixture containing about 2 to about 10 wt. % cyclohexylbenzene being taken overhead.

The continuous production of cyclohexanone by maintaining a body of a mixture of it and phenol having dispersed therein finely divided palladium catalysts at an elevated temperature, while continuously passing hydrogen into said body to catalytically hydrogenate the phenol to cyclohexanone and while continuously passing a gas through said body to remove cyclohexanone as vapors free of catalysts substantially as formed, while introducing phenol into said body to maintain the body substantially constant, is disclosed in U.S. Pat. 2,857,432 issued Oct. 21, 1958.

Any catalytic hydrogenation temperature can be employed which provides the desired degree of catalytic selectivity and efficiency for the hydrogenation of the phenol in the feedstock without substantially hydrogenating the cyclohexylbenzene. The hydrogenation temperature will generally be within the range of about 20° to about 300° C. and preferably will be in the range of about 100° to about 200° C.

The catalytic hydrogenation of this invention can be carried out at any hydrogenation pressure wherein the desired hydrogenation occurs. Generally, hydrogen pressure for batch reactions are within the range of about 0 to about 5000 psig (0 to 34470 kPa). Preferably, hydrogen pressures within the range of about 50 to about 500 psig (345 to 3447 kPa) are employed.

Diluents can be utilized in the catalytic hydrogenation of this invention but are not now preferred. When diluents are used they should remain unreactive under the conditions used. Generally speaking, the choice of the diluent may often be determined based on the difference in boiling points expected between the hydrogenation products and the diluent so as to facilitate separation of the components of the reaction mixture. Suitable diluents can be selected from the class consisting of alcohols containing from 1 to 12 carbon atoms per molecule, acyclic and cyclic ethers having four to 12 carbon atoms per molecule, saturated hydrocarbons having 4 to 12 carbon atoms per molecule, carboxylic acids containing from 1 to 8 carbon atoms per molecule and mixtures thereof. Examples of alcohol diluents include methanol, ethanol, 2-propanol, 1-dodecanol, and the like, and mixtures thereof. Examples of saturated hydrocarbons include butane, pentane, hexane, cyclopentane, cyclohexane, cyclododecane, and the like, and mixtures thereof. Examples of ethers include diethyl ether, 1,3-dioxane, 1,4-dioxane, tetrahydrofuran, and the like, and mixtures thereof. Examples of carboxylic acids include acetic acid, and propionic acid and the like, and mixtures thereof. The weight ratio of feedstock to diluent will generally range from about 0.001:100 up to about 50:100 and will preferably range from about 0.01:100 up to about 30:100.

The time utilized in the hydrogenation of this invention will depend on the level of the catalyst utilized, reaction temperature and reaction pressure and can range from a few minutes to several hours.

Intimate contact of the reactants and catalyst is of benefit in the hydrogenation reaction of this invention, and conventional means of good mixing by stirring, shaking and the like can be employed as taught in the prior art.

Any catalyst that gives the desired hydrogenation results can be utilized in this invention. Examples of suitable catalysts include palladium and platinum. The catalyst can be used as the finely divided metal, but for economy and for ease of recovery and reuse, it is preferably deposited on an inert carrier or support. Suitable supports include carbon, alumina, silica, kieselguhr and the like, and mixtures thereof. The catalyst can be used in any amount that is effective in catalyzing the desired hydrogenation reaction and will generally be utilized in amounts, based on elemental metal, from about 0.0001 up to about 5, preferably from about 0.001 to about 1 weight % of the feed stream.

When a support is employed, the elemental metal will generally be in the range of about 0.1 to about 50 and preferably in the range of about 0.2 to about 10 weight % based on the weight of the support. The catalyst can also contain promotors such as inorganic alkali metal compounds. Examples of suitable alkali metal compounds include sodium hydroxide, lithium hydroxide, potassium hydroxide, sodium carbonate, potassium carbonate, sodium chloride, potassium chloride, and the like and mixtures thereof.

The hydrogenation of this invention can be conducted either as a batch or as a continuous reaction using methods known in the art.

The continuous process can be carried out at any suitable liquid hourly space velocity (LHSV). However, the LHSV will generally be within the range of about 0.01 to about 10, more preferably from about 0.1 to about 4, volumes of feed stream plus diluent per volume of catalyst (including the volume of any catalyst support if any is present).

It is also preferred that oxygen and water be excluded from the hydrogenation reaction of this invention.

At the conclusion of the hydrogenation reaction of this invention, the reaction effluent can be processed through a conventional separation means to recover the diluent and products. The reaction effluent can be filtered to remove the catalyst and then is fractionally distilled to separate the products of the hydrogenation.

An overhead stream containing cyclohexanone substantially free of phenol and a bottom stream containing cyclohexylbenzene are obtained. The cyclohexylbenzene is recycled to the cyclohexylbenzene oxidation stage.

EXAMPLES

In the following examples, the batch hydrogenations were carried out in a 300 ml stainless steel autoclave equipped with a variable speed stirrer. In each run, the autoclave was charged with the catalyst and reactants, flushed with nitrogen, and pressured with hydrogen. The autoclave was heated to the desired temperature and the hydrogen pressure was maintained at a constant value via a regulator. Samples were withdrawn periodically from the autoclave reaction mixture and analyzed by gas-liquid phase chromatography (glpc).

The mixtures to be separated were prepared from cyclohexylbenzene (from the reductive alkylation of benzene), commercial, reagent grade cyclohexanone, and purified phenol. The purified phenol was prepared by treating phenol with 0.1 weight % sodium hydroxide and 0.1 weight % ethylenediaminetetraacetic acid (EDTA) and distillation.

The palladium on carbon (Pd/C) catalyst is a commercial catalyst containing 5 weight % palladium with the percentage being based on the weight of the support. The other catalysts were prepared for use in the examples by depositing sodium hydroxide from an aqueous solution on a commercial 5 weight % Pd/C catalyst. The prepared catalysts were oven dried and reduced in the presence of hydrogen.

EXAMPLE I

Two batch runs were carried out to demonstrate the process of this invention for the hydrogenation of a mixture containing 67 weight % phenol, 28 weight % cyclohexanone, and 5 weight % cyclohexylbenzene (CHB). This mixture (100 g.) was hydrogenated at 80 psig (552 kPa) with a stirring rate of 2000 rpm in the presence of 0.2 g of a catalyst containing 5 weight % palladium and 0.29 weight % sodium on a carbon support. The temperatures utilized and the results obtained in these runs are shown in Table I.

Table I

| Run No. | Reaction Temp., °C. | Reaction Time, Hours | Phenol Conv. Wt. % | Selectivity to Cyclohexanone[a] Weight % | CHB Recovered Weight % |
|---|---|---|---|---|---|
| 1 | 185° | 0.5 | 74 | 98 | 98 |
|   |      | 1.0 | 95 | 97 | 96 |
|   |      | 1.5 | 99 | 97 | 90 |
| 2 | 160° | 1   | 65 | 96 | 98 |
|   |      | 2   | 96 | 97 | 94 |
|   |      | 3   | 99 | 97 | 91 |

[a]Selectivity to cyclohexanone based on the amount of phenol converted.

The results of these runs show that a mixture containing cyclohexanone, phenol, and the cyclohexylbenzene can be hydrogenated at either 185° or 160° C. with a high level of conversion of phenol and with a high level of selectivity to cyclohexanone to yield a mixture of cyclohexanone and cyclohexylbenzene that can be easily separated by fractional distillation.

EXAMPLE II

Two more batch runs were carried out to demonstrate the hydrogenation of this invention utilizing different catalysts, catalyst levels, and temperatures. The feed mixture and the hydrogenation pressure were the same as described in Example I. In run 3, 0.1 g. of the same catalyst as in Example I was utilized. In run 4, 0.3 g. of a 5% palladium on carbon catalyst was used. The reaction temperatures and results of these runs are shown below in Table II.

Table II

| Run No. | Reaction Temp., °C. | Reaction Time, Hours | Phenol Conv. Wt. % | Selectivity to Cyclohexanone[a] Weight % | CHB Recovered Weight % |
|---|---|---|---|---|---|
| 3 | 185° | 1.5 | 78 | 97 | 97 |

Table II-continued

| Run No. | Reaction Temp., °C. | Reaction Time, Hours | Phenol Conv. Wt. % | Selectivity to Cyclohexanone[a] Weight % | CHB Recovered Weight % |
|---|---|---|---|---|---|
|   |      | 2.5 | 94 | 97 | 96 |
|   |      | 3.5 | 98 | 96 | 93 |
| 4 | 141° | 1.5 | 73 | 98 | 97 |
|   |      | 2.5 | 92 | 97 | 95 |
|   |      | 3.5 | 97 | 96 | 93 |
|   |      | 4.5 | 99 | 96 | 89 |

[a]See footnote (a) of Table I.

The results of these runs show that the phenol-cyclohexanone-cyclohexylbenzene mixture can be hydrogenated to a simpler mixture containing cyclohexanone and cyclohexylbenzene at several reaction temperatures and catalyst levels.

EXAMPLE III

Two batch hydrogenation runs were carried out to demonstrate the effect of stirring speed on conversion rate for the hydrogenation of 100 g. of a mixture containing 70 weight % phenol and 30 weight % cyclohexanone. The hydrogenation conditions were 80 psig (552 kPa) and 185° C. The catalyst in each run was 0.2 g. of a 5 weight % Pd/C catalyst containing 2900 ppm sodium. The results of runs at 1000 and 2000 rpm stirrer speed are shown in Table III.

Table III

| Run No. | Stirrer Speed, rpm | Reaction Time, Hours | Phenol Conv. Weight % | Selectivity to Cyclohexanone[a] Weight % |
|---|---|---|---|---|
| 8 | 1000 | 1.5 | 36 | 95 |
|   |      | 2.5 | 62 | 96 |
|   |      | 3.5 | 98 | 97 |
| 9 | 2000 | 1.0 | 86 | 96 |
|   |      | 1.5 | 99 | 97 |
|   |      | 2.0 | 99 | 95 |

[a]See footnote (a) of Table I.

The results of these runs show that the higher stirrer speed (2000 rpm in run 9) resulted in a higher phenol conversion at 1.5 hours reaction time than at the lower stirrer speed (100 rpm in run 8).

The boiling point of cyclohexanone is 156.7° C.; that of cyclohexylbenzene is 237.5° C., at atmospheric pressure.

Reasonable variation and modification are possible within the scope of the foregoing disclosure and the appended claims to the invention the essence of which is that a mixture containing cyclohexylbenzene, cyclohexanone and phenol can be worked up or separated so as to recover cyclohexylbenzene, which can then be used, by subjecting the mixture to hydrogenation conditions to convert phenol in the mixture to cyclohexanone, and then separating the cyclohexanone and cyclohexylbenzene by conventional methods as by distillation.

I claim:

1. A process for the improved production of cyclohexanone which comprises, in a zone, oxidizing cyclohexylbenzene to produce cyclohexylbenzene hydroperoxide, acid-cleaving the cyclohexylbenzene hydroperoxide thus obtained, thus obtaining a mixture of cyclohexylbenzene, phenol and cyclohexanone, subjecting the mixture to hydrogenation to convert selectively the phenol to cyclohexanone, fractionally separating the cyclohexanone and cyclohexylbenzene and returning the cyclohexylbenzene to said zone.

2. A process according to claim 1 wherein the hydrogenation temperature will be within the approximate range of from about 20° to about 300° C. and a catalyst effective to hydrogenate the phenol is used.

3. The recovery of cyclohexylbenzene from a mixture containing it together with phenol and cyclohexanone which comprises subjecting the mixture to hydrogenation conditions selectively to convert phenol to cyclohexanone and separating the cyclohexylbenzene and cyclohexanone.

4. A process according to claim 3 wherein the cyclohexylbenzene and cyclohexanone are separated by distillation.

5. A process according to claim 3 wherein the hydrogenation temperature will be within the approximate range of from about 20° to about 300° C. and a catalyst effective to hydrogenate the phenol is used.

* * * * *